United States Patent [19]

Huber et al.

[11] Patent Number: 6,001,228
[45] Date of Patent: Dec. 14, 1999

[54] DEVICE FOR PERFORMING MEASUREMENTS IN FLUIDS

[75] Inventors: Wolfgang Huber, Lieboch; Andreas Dolezal, Graz; Bernhard Schaffar, Graz; Christoph Ritter, Graz, all of Australia

[73] Assignee: AVL Medical Instruments AG, Schaffhausen, Switzerland

[21] Appl. No.: 08/935,536

[22] Filed: Sep. 23, 1997

[30] Foreign Application Priority Data

Oct. 30, 1996 [AU] Australia .................................. 1906/96

[51] Int. Cl.⁶ ...................................................... G01N 27/26
[52] U.S. Cl. .................... 204/403; 422/82.06; 435/288.5; 204/416
[58] Field of Search ...................................... 204/416, 418, 204/419, 403; 422/82.06, 948; 435/288.5

[56] References Cited

U.S. PATENT DOCUMENTS 5,284,568 2/1994 Pace et al. .
5,520,787 5/1996 Hanagan et al. .
5,522,978 6/1996 Pace et al. ............................... 204/418

FOREIGN PATENT DOCUMENTS 0690134 1/1996 European Pat. Off. .

*Primary Examiner*—T. Tung
*Assistant Examiner*—Jennifer C. McNeil
*Attorney, Agent, or Firm*—Watson Cole Grindle Watson, P.L.L.C.

[57] ABSTRACT

A device for performing electrochemical and/or optical measurements in fluids, includes a sensor part of substantially planar configuration carrying a plurality of sensors that are connected to conductive paths; a cover part, which includes a groove-shaped measuring channel through which the fluid will flow; and a sealing element positioned between the sensor part and the cover part for sealing the measuring channel. The cover part includes grooves which extend in parallel with the measuring channel and which define respective ridges between the grooves and the measuring channel, and the sealing element substantially includes guiding bodies which are retained in the grooves of the cover part and are provided with integrally molded narrow sealing lips protruding in the area of the ridge. The sensor part and the cover part are joined by a plurality of locking elements which are distributed along the measuring channel.

10 Claims, 5 Drawing Sheets

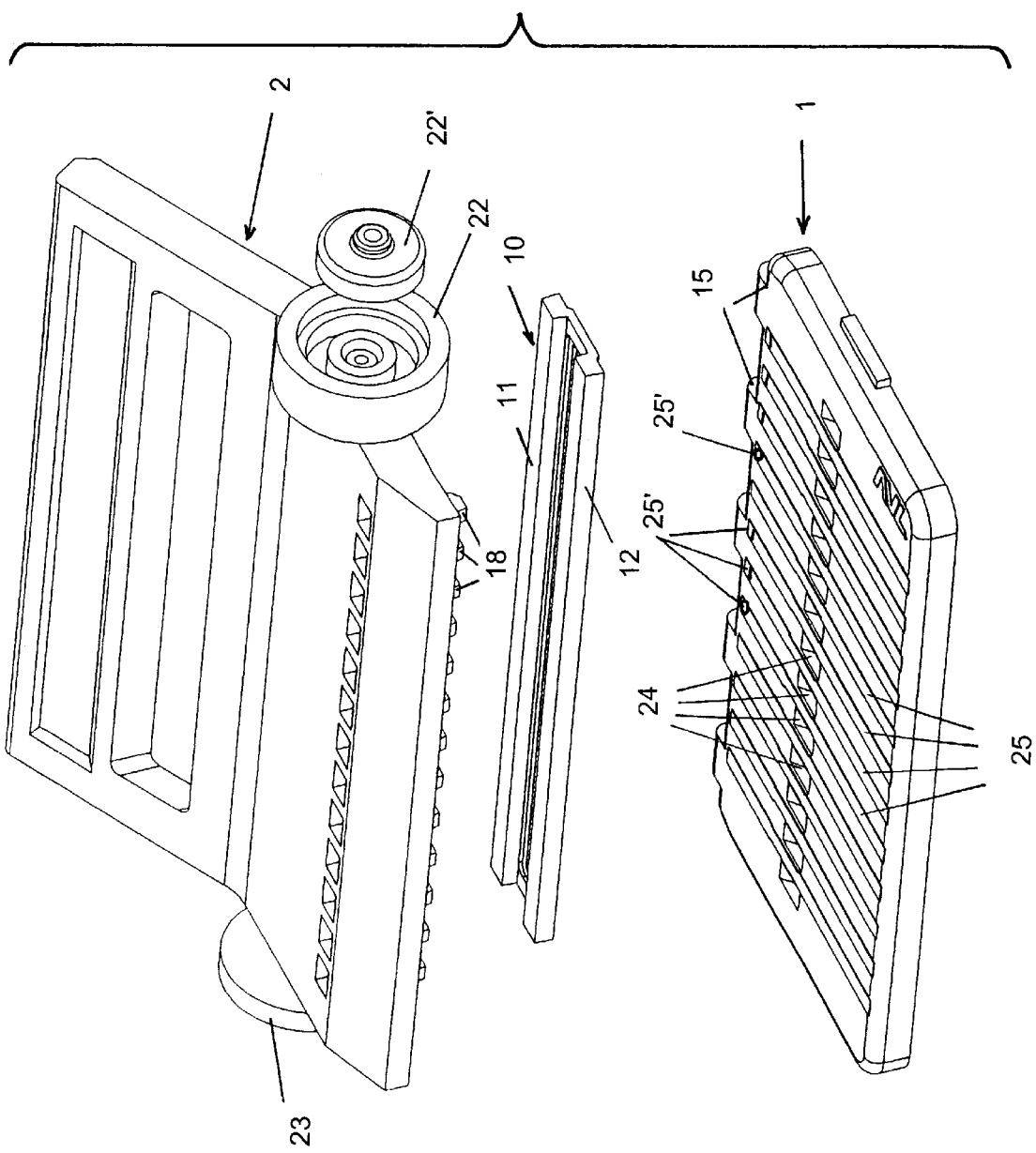

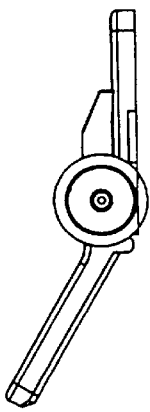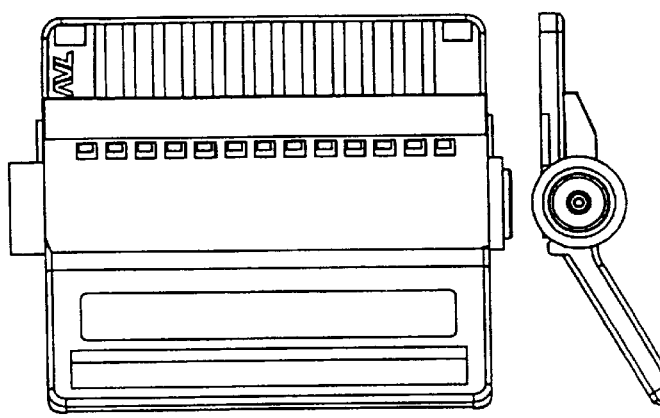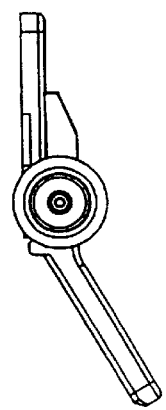
Fig. 14  Fig. 12  Fig. 13
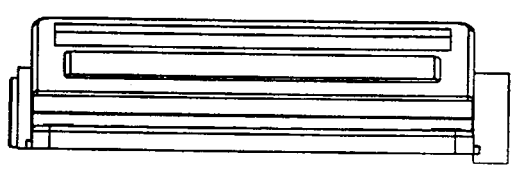
Fig. 16  Fig. 17
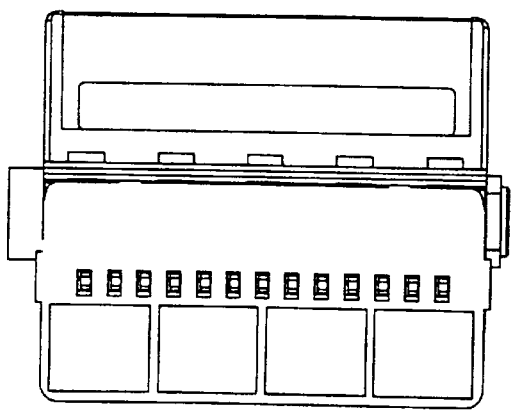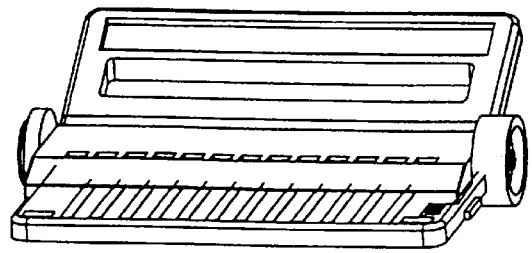
Fig. 15  Fig. 18

DEVICE FOR PERFORMING MEASUREMENTS IN FLUIDS

BACKGROUND OF THE INVENTION

The invention relates to a device for performing electrochemical and/or optical measurements in fluids, including the following elements;

a sensor part of substantially planar configuration, which carries a plurality of sensors that are possibly connected to conductive paths;

a cover part, in which a groove-shaped measuring channel is formed through which the fluid will flow;

a sealing element positioned between the sensor part and the cover part for sealing the measuring channel, which is.

Electrochemical and optical measuring processes are generally implemented in measuring chambers which are furnished with electrodes and/or optodes. The present invention is primarily concerned with devices in which the measuring chamber is configured as a flow channel through which the sample medium, such as blood, is drawn. The flowing medium is brought into contact with different sensors and electrodes in order to enable the measuring process to be performed.

DESCRIPTION OF THE PRIOR ART

In U.S. Pat. No. 5,284,568 a measuring assembly is described in which a number of sensor elements are positioned in a measuring channel. The sensors are applied on a supporting plate constituting a boundary face of the measuring channel.

The channel is further defined by a cover member made of substantially elastomeric material. In many applications the filling behavior and biocompatibility of such elastomers are unsatisfactory, thus impairing the accuracy of the measuring process. Moreover, the geometry of the measuring channel is not fully reproducible due to potential deformations. In the instance of biosensors, which exhibit a most sensitive response to changes in filling behavior or filling volume, such as in kinetic measurements, use of the known assembly will lead to disadvantages. In addition, the known assembly is costly since electrical and liquid connections are difficult to establish in the elastomer.

In EP 0 690 134 A1 an electrochemical flow cell is described in which a measuring chamber is formed as a recess in a component, the flow cell being closed by an electrode plate on the opposite side. The unit is sealed by a sealing element with an opening substantially corresponding to the recess of the measuring chamber. These elements are contained in a multipart housing which is sealed by welding. In this type of assembly a large part of the surface of the measuring chamber is made of elastomeric material, such that the same disadvantages are encountered as described above.

In U.S. Pat. No. 5,520,787, finally, a flow cell is presented, which is defined by two substantially plane plates. Between the two plates a spacer is provided which consists of a layer of sealing material. The flow channel is formed by a suitable recess in this layer. Apart from the above disadvantaqes, it should be noted in this context that the position of the lateral edge of the flow channel is not accurately defined. Moreover, as the individual components of this assembly are glued together, the risk of contact between adhesive layer and sample medium or sensors cannot be excluded. In certain measuring processes such contact will be most undesirable, however.

SUMMARY OF THE INVENTION

It is an object of the present invention to avoid these disadvantages and to propose a device of the kind described above, which is easy to manufacture and ensures an accurate and reproducible geometry of the measuring channel. The portion of the surface of the measuring channel which is made of elastomeric materials should be kept as small as possible.

According to the invention this object is achieved by providing that grooves be formed in the cover part, which run parallel to the measuring channel, a ridge being provided between each groove and the measuring channel, and that the sealing element substantially includes guiding bodies which are retained in the grooves of the cover part and are provided with integrally molded narrow sealing lips protruding in the area of the ridge, and further that the sensor part and the cover part are joined by a plurality of locking elements which are distributed along the measuring channel.

By combining the above characteristics the thickness of the sealing layer may be kept very small in the area of the measuring channel, which will have the advantages described above. The snap connection described by the invention will permit a uniform pressure between the sensor part and the cover part, which will reliably prevent any leaks. The sealing element is securely positioned in the grooves of the cover part, such that the geometry of the measuring channel is accurately defined.

The device of the invention is suitable for electrochemical as well as optical sensors or combinations thereof, i.e., above all biosensors, electrolyte sensors, blood gas sensors.

The locking elements between the sensor part and the cover part may be configured such that they cannot be released without being destroyed, once they are engaged. In another variant the locks may be released during normal operation. In the former instance the entire assembly is a disposable device to be discarded as a whole even though it may be designed for repeated use.

It is provided in a preferred variant that locking faces be provided integrally with the cover part on one side of the measuring channel, which faces are engaged by retaining noses of the sensor part in the assembled state, and that snaps be provided on the opposite side of the measuring channel between every two conductive paths, in order to join sensor part and cover part. In this manner a particularly stable and rigid assembly is obtained which will ensure maximum reliabiality of operation.

The alignment of the individual components may be improved by providing centering pins on the cover part which are designed to engage in corresponding bores in the sensor part.

Special preference is given to a variant in which the sealing lip has a thickness of 10 to 500 $\mu$m, i.e., 100 to 200 $\mu$m, preferably.

BRIEF DESCRIPTION OF THE DRAWINGS

The invention will be further described with reference to the accompanying drawings, in which

FIG. 5 is an axonometric exploded view of a variant of the device described by the invention.

FIGS. 12 to 18 show various views of the device of the invention; FIG. 12 from above, FIG. 13 from the left, FIG. 14 from the right, FIG. 15 from below, FIG. 16 a front view, FIG. 17 a rear view, FIG. 18 an oblique view.

DETAILED DESCRIPTION OF PREFERRED EMBODIMENTS

Figure 1:
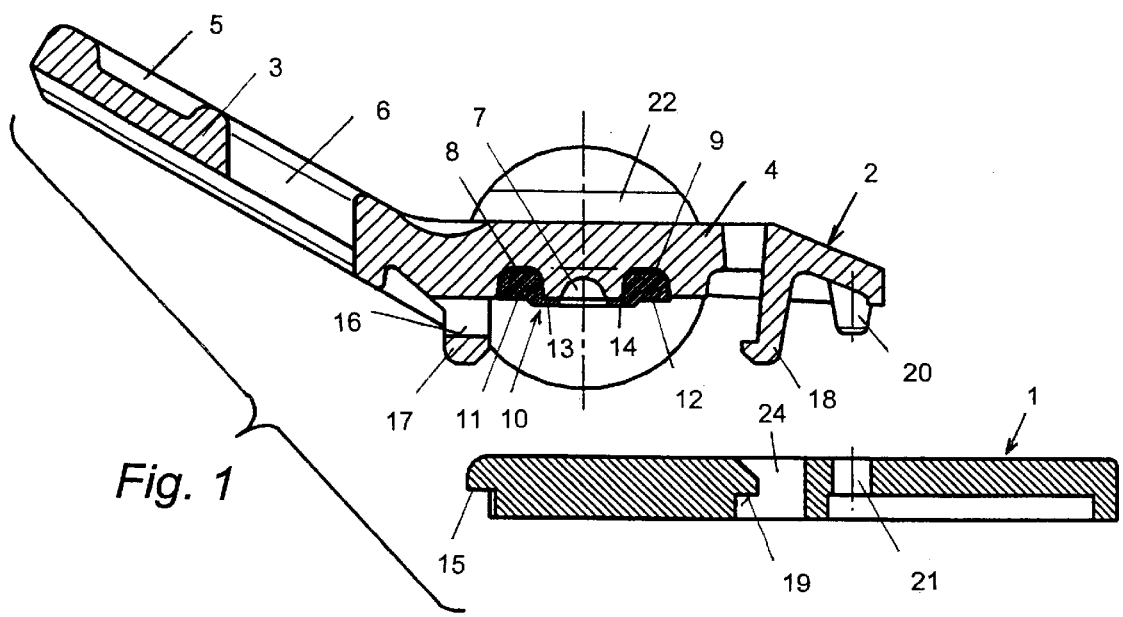
FIG. 1 is a section through a variant according to the invention showing the cover part detached from the sensor part.

The device of the invention substantially includes a sensor part 1 and a cover part 2. The sensor part 1 is of substantially planar configuration. For ease of manipulation the cover part 2 is provided with a handle 3, which is upwardly projecting from the actual covering area 4 at an obtuse angle and has a gripping recess 5 and a hole 6 for better gripping of the cover part 2. In the covering area 4 the measuring channel 7 is formed as a groove which extends in longitudinal direction and is open towards the sensor part 1. Parallel to the measuring channel 7 are provided grooves 8 and 9 which are designed to hold a sealing element 10. The sealing element 10 includes guiding bodies 11 and 12 which are retained in grooves 8 and 9. The guiding bodies 11, 12 each have a narrow sealing lip 13, 14 whose thickness is about 150 $\mu$m. By means of sealing lips 13, 14 the actual seal is established between the sensor part 1 and the cover part 2.

Figure 2:
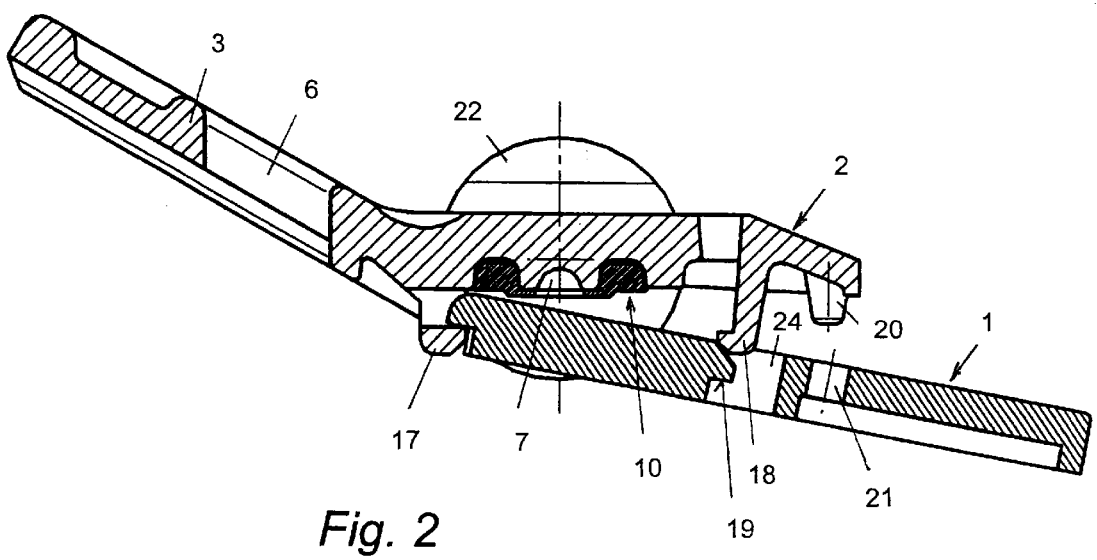
FIG. 2 is a section corresponding to FIG. 1, showing the cover part during fastening on the sensor part.
Figure 3:
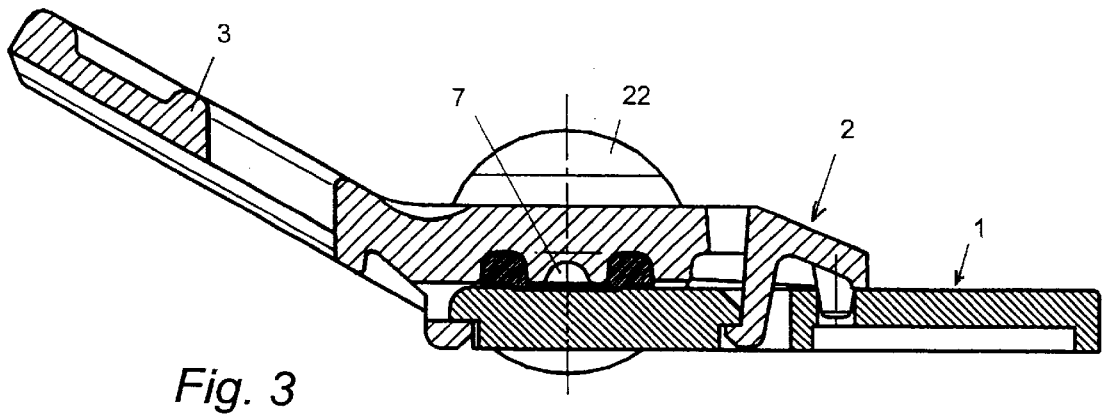
FIG. 3 is a section corresponding to FIGS. 1 and 2, showing the device in the assembled state.
Figure 4:
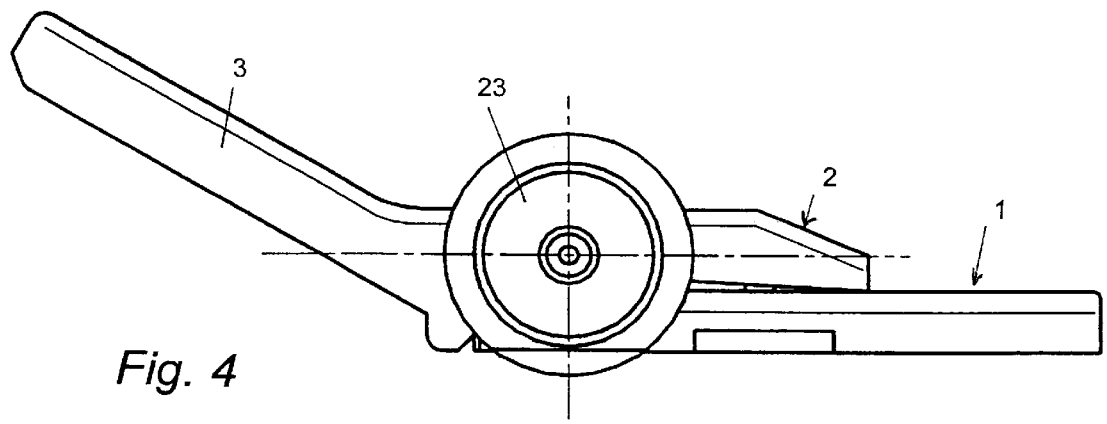
FIG. 4 is a lateral view of the device.

The connection between the sensor part 1 and the cover part 2 is established as show in FIG. 2 and 3. A series of retaining noses 15, which are positioned in a straight line along one edge of the sensor part 1, are placed on corresponding locking faces 16. The locking faces 16 are formed on the cover part 2 in a downwardly projecting ledge 17 extending in longitudinal direction. After the retaining noses 15 have been placed on the locking faces 16, the sensor part 1 and the cover part 2 are tilted towards each other using the retaining nose 15 as a pivot. During this movement snaps 18, which are protruding downwards from the cover part 2, will engage with locking faces 19, which are provided in openings 24 of the sensor part 1. Accurate alignment of sensor part 1 and cover part 2 is achieved with the use of centering pins 20, which are downwardly protruding from the cover part 2 and will engage in centering bores 21 at the sensor part 1 in the assembled state.

The medium to be analyzed is introduced aid carried off via connections 22 and 23, respectively, which are molded integral with the cover part 2 at the ends of the measuring channel 7.

FIG. 5 is an exploded view of the overall configuration of the device described by the invention. As is seen, a total of twelve conductive paths 25 are provided on the surface of the sensor part 1, each of them leading to sensors 25'. The conductive paths 25 and the sensors 25' can be applied to the planar surface by means of conventional thick and/or thin film technologies, such as sputtering, screen-printing or dispensing. The conductive paths are simultaneously used for contacting the sensors. Between every two conductive paths 25 there are openings 24 through which the snaps 18 may be inserted to engage with the locking faces 19 (not shown in FIG. 5). 22' refers to a sealing element in connection 22.

Figure 7:
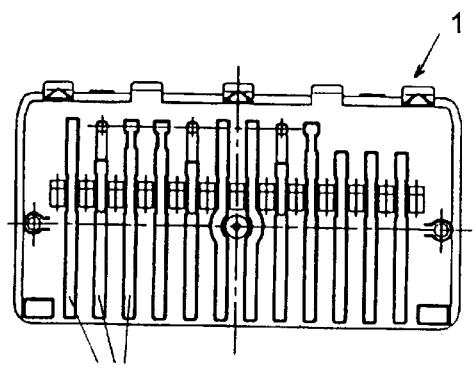
FIGS. 6 to 11 show the sensor part in successive stages of its manufacturing process.
Figure 6:
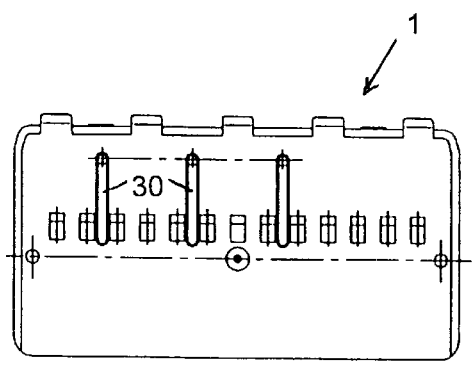
Figure 9:
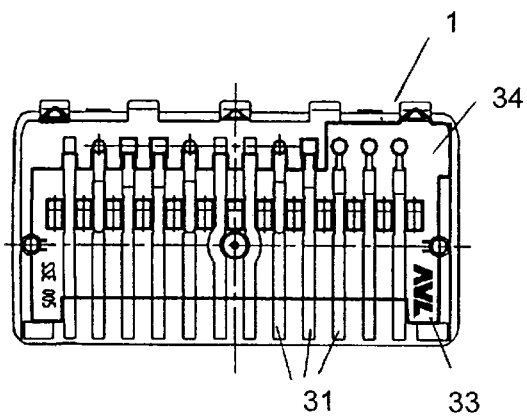
Figure 8:
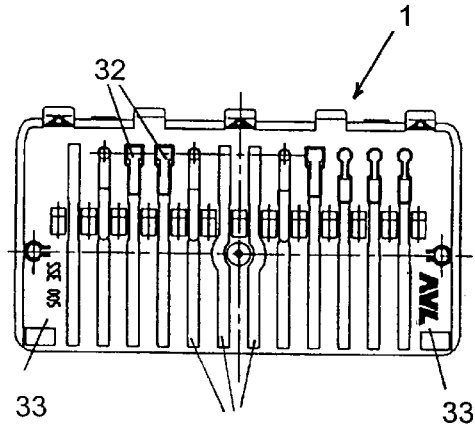
Figure 11:
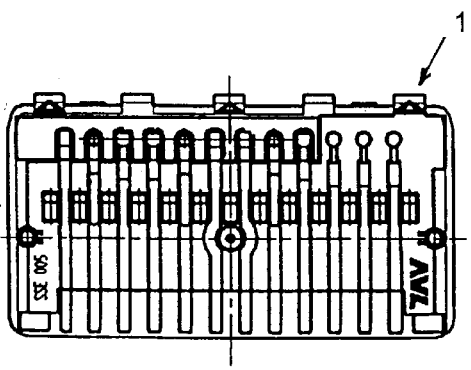
Figure 10:
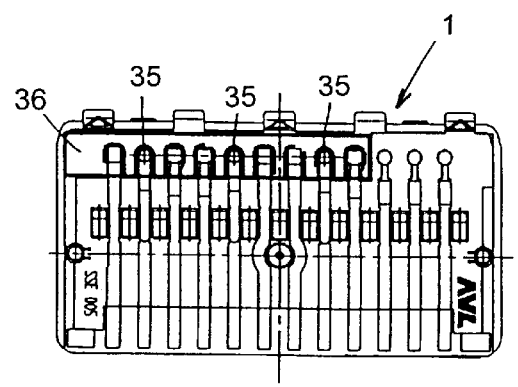

FIG. 6 to 11 show the successive stages of the manufacturing process for sensor part 1. First of all gold paths 30 are sputtered on (FIG. 6). In FIG. 7 silver/silver chloride paths 31 are produced by screen-printing. In FIG. 8 carbon coats 32 and lettering 33 are applied to the sensor part 1 using screen printing techniques. In FIG. 9 the screen-printed insulating layer 34 (dielectric paste) is applied. FIG. 10 shows the assembling of the sensor together with inserts 35 and the welding of the PC membrane 36; FIG. 11, finally, presents the fully assembled sensor part 1.

The present invention provides a measuring chamber for planar sensors of a most simple design, in which the measuring channel has an accurately defined geometry and is largely free from undesired materials. The sensor part 1 and the cover part 2 may be configured as transparent or translucent units in order to make the sample visible and permit illumination of the assembly from below, if desired. The measuring channel has a length of 1 to 5 cm, preferably about 2 to 3 cm, and a width of 1 to 3 mm, and a depth or 0.5 to a 3 mm. It is preferred that both width and depth be 1.5 mm. In this way the measuring channel has a volume of 5 to 200 $\mu$l preferably 20 to 50 $\mu$l The device proposed by the invention is excellently suited for diagnostic purposes, preferably analyses of blood plasma, serum and urine.

We claim:

1. Device for performing measurements in fluids, said device comprising:

a sensor part of substantially planar configuration which carries on an upper surface thereof a plurality of sensors, said sensor part providing a plurality of first locking faces along a side thereof;

a cover part which provides on a lower surface thereof a groove-shaped measuring channel for holding said fluid, grooves on opposite sides of said measuring channel and which extend in parallel with said measuring channel so as to form a respective ridge between each groove and the measuring channel, a plurality of retaining noses on one side of said measuring channel for engagement with respective first locking faces of said sensor part when said cover part is attached to said sensor part, and a plurality of snap means on a second side of said measuring channel to snap fit with said sensor part to fixedly attach said cover part to said sensor part; and a sealing element positioned between said sensor part and said cover part when attached together for sealing said measuring channel, said sealing element comprising guiding bodies which respectively fill said grooves and integrally molded narrow sealing lips protruding over portions of said ridges.

2. Device according to claim 1, wherein said sensor part carries a plurality of electrochemical sensors being connected to conductive paths provided on said sensor part.

3. Device according to claim 2, wherein said sensor part carries at least one optical sensor.

4. Device according to claim 1, wherein said sensor part carries a plurality of optical sensors.

5. Device according to claim 1, wherein centering pins are provided on said cover part, which are designed to engage in corresponding bores in said sensor part.

6. Device according to claim 1, wherein each of said sealing lips has a thickness of 10 to 500 $\mu$m.

7. Device according to claim 6, wherein each of said sealing lips has a thickness of 100 to 200 $\mu$m.

8. Device according to claim 1, wherein said retaining noses are formed by projections which extend away from a side edge of said sensor part.

9. Device according to claim 1, wherein said sensor part includes a plurality of openings which define a plurality of second locking faces which said snap means contact when said cover part is fixedly attached to said sensor part.

10. Device according to claim 1, wherein said cover part includes a ledge which extends away from said lower surface thereof and which includes a plurality of openings therein to provide said plurality of first locking faces.

* * * * *

UNITED STATES PATENT AND TRADEMARK OFFICE
CERTIFICATE OF CORRECTION

PATENT NO. : 6,001,228
DATED : December 14, 1999
INVENTOR(S) : Wolfgang Huber et al.

It is certified that error appears in the above-identified patent and that said Letters Patent is hereby corrected as shown below: On title page, item

[75] Inventors: Wolfgang Huber, Lieboch; Andreas
Dolezal, Graz; Bernhard Schaffar,
Graz; Christoph Ritter, Graz, all of Austria

[30] Foreign Application Priority Data
Oct. 30, 1996 [AT] Austria..................................................................1906/96

Signed and Sealed this

Eighth Day of August, 2000

Attest:

Q. TODD DICKINSON

*Attesting Officer*  *Director of Patents and Trademarks*